United States Patent
Hodges

(10) Patent No.: US 8,141,701 B2
(45) Date of Patent: Mar. 27, 2012

(54) PACK FOR TOBACCO INDUSTRY PRODUCTS

(75) Inventor: Paul Hodges, London (GB)

(73) Assignee: British American Tobacco (Investments) Limited, London (GB)

( * ) Notice: Subject to any disclaimer, the term of this patent is extended or adjusted under 35 U.S.C. 154(b) by 0 days.

(21) Appl. No.: 13/202,811

(22) PCT Filed: Jan. 15, 2010

(86) PCT No.: PCT/EP2010/050482
§ 371 (c)(1), (2), (4) Date: Aug. 24, 2011

(87) PCT Pub. No.: WO2010/097252
PCT Pub. Date: Sep. 2, 2010

(65) Prior Publication Data
US 2012/0012479 A1    Jan. 19, 2012

(30) Foreign Application Priority Data
Feb. 24, 2009 (GB) .................................. 0903069.3

(51) Int. Cl.
*B65D 85/10* (2006.01)
(52) U.S. Cl. ....................... 206/268; 206/273; 206/459.1
(58) Field of Classification Search .................. 206/204, 206/242, 265, 268, 270, 273, 459.1; 229/87.12, 229/87.13, 87.14, 160.1
See application file for complete search history.

(56) References Cited

U.S. PATENT DOCUMENTS

| | | | | |
|---|---|---|---|---|
| 4,717,017 A | * | 1/1988 | Sprinkel et al. | 206/264 |
| 5,249,676 A | * | 10/1993 | Ashcraft et al. | 206/264 |
| 5,938,018 A | * | 8/1999 | Keaveney et al. | 206/268 |
| 6,612,429 B2 | * | 9/2003 | Dennen | 206/268 |
| 7,600,668 B2 | * | 10/2009 | Pham | 229/87.05 |
| 2006/0278542 A1 | * | 12/2006 | Pham et al. | 206/268 |
| 2007/0193892 A1 | | 8/2007 | Tanbo et al. | |
| 2009/0071852 A1 | * | 3/2009 | Negrini | 206/268 |

FOREIGN PATENT DOCUMENTS

| | | |
|---|---|---|
| DE | 1517263 A1 | 9/1969 |
| DE | 102006029092 A1 | 12/2007 |
| FR | 2864428 A1 | 7/2005 |
| JP | 2002291843 A | 3/2001 |
| WO | WO 2008/148702 A1 | 12/2008 |

OTHER PUBLICATIONS

International Search Report and Written Opinion, mailed Apr. 7, 2010 for PCT Application No. PCT/EP2010/050482, filed Jan. 15, 2010. International Preliminary Report on Patentability, mailed Mar. 22, 2011 for PCT Application No. PCT/EP2010/050482, filed Jan. 15, 2010.
Search Report, mailed Apr. 14, 2009 for GB application No. GB0903069.3, filed Feb. 24, 2009.

* cited by examiner

*Primary Examiner* — Luan K Bui
(74) *Attorney, Agent, or Firm* — Chadbourne & Parke LLP; Walter G. Hanchuk

(57) ABSTRACT

A pack for tobacco industry products such as menthol cigarettes, comprises a housing (1) defining an enclosure containing tobacco industry products (4) and a pad (34) disposed in or on the pack, impregnated with the substance for altering characteristics of the tobacco industry products, such as a menthol flavorant, and a removable strip (32), attached to the pad so that when removed, the substance is released into the pack from the carrier to be adsorbed by the cigarettes. Thus, menthol can be released from the pad into the pack after opening by the consumer, by removal of the strip to boost the level of menthol flavorant in the cigarettes.

18 Claims, 6 Drawing Sheets

PACK FOR TOBACCO INDUSTRY PRODUCTS

CLAIM FOR PRIORITY

This application is a National Stage Entry entitled to and hereby claims priority under 35 U.S.C. §§365 and 371 to corresponding PCT Application No. PCT/EP2010/050482, filed Jan. 15, 2010, which in turn claims priority to British Application Serial No. GB 0903069.3, filed Feb. 24, 2009. The entire contents of the aforementioned applications are herein expressly incorporated by reference.

FIELD OF THE INVENTION

The present invention relates to a pack for tobacco industry products adapted to release a substance, for example to refresh or enhance the products with the substance.

BACKGROUND

The present invention is described herein with reference to "tobacco industry products". A tobacco industry product as referred to herein is any item made in, or sold by the tobacco industry, typically including a) cigarettes, cigarillos, cigars, tobacco for pipes or for roll-your-own cigarettes, (whether based on tobacco, tobacco derivatives, expanded tobacco, reconstituted tobacco or tobacco substitutes); b) non-smoking products incorporating tobacco, tobacco derivatives, expanded tobacco, reconstituted tobacco or tobacco substitutes such as snuff, snus, hard tobacco, and heat-not-burn products; and c) non-tobacco products such as for example aerosol delivery devices, inhalers, lozenges and gum. This list is not intended to be exclusive, but merely illustrates a range of products which are made and sold in the tobacco industry.

Menthol-flavoured cigarettes are well-known in the art and comprise a tobacco-based cigarette to which menthol flavouring is added. When consumed, the user experiences the taste of menthol.

Cigarettes are contained and sold to consumers in cigarette packs which are typically sealed during manufacture to maintain the freshness of the product contained therein. However, once the pack is opened, the product's freshness deteriorates over time. The tobacco of the cigarettes can become undesirably dry once the pack is opened. Also, the cigarettes may be provided with a flavourant during manufacture, such as menthol, and over time, the menthol flavouring may escape from the product with the result that the consumer experiences menthol levels in the products which are below those prescribed by the manufacturer. Eventually, the menthol flavouring of products contained in an opened pack can be lost to an extent where the article becomes undesirable to the consumer.

SUMMARY OF THE INVENTION

The invention provides a pack for tobacco industry products, comprising a housing defining an enclosure in which a plurality of tobacco industry products can be accommodated, and a carrier disposed in or on the pack, said carrier being arranged to accommodate a substance for altering characteristics of the tobacco industry products when in the pack, wherein the carrier comprises a pad impregnated with the substance, and a removable strip, attached to the carrier so that when removed, the substance is released into the pack from the carrier to be adsorbed by the tobacco industry products.

Thus, a substance such as flavouring substance can be incorporated into the pack for absorption by tobacco industry products disposed therein for example to replenish or enhance them for the time when the article is to be consumed.

The pack may comprise an outer shell, an inner frame and a lid, the pad and the strip being disposed between the outer shell and the inner frame and the strip having a portion extending into the lid so that when opened, the strip can be gripped manually and removed from engagement with the pad to release the substance from the pad.

The pad may be attached to the outer shell, and a membrane may be provided between the outer shell and the pad to prevent the substance in the pad from passing into the outer shell.

An aperture configuration may be provided in the outer shell overlying the strip to provide a visual indication of whether the strip has been removed from the pack. The inner frame may be of a different appearance from the strip in a region underlying the aperture configuration in the outer shell.

A wick may be provided to convey the substance from the pad within the enclosure and the wick may comprise a portion of the housing. The wick may be disposed to direct to the substance released from the carrier to a predetermined portion of the enclosure. The inner frame may be permeable to the substance accommodated in the carrier and act as the wick.

The substance accommodated in the carrier may comprise a flavouring substance such as menthol, or a substance such as water to refresh dry and stale products without additional flavouring thereof.

The invention also includes a kit for and a method of manufacturing the pack.

BRIEF DESCRIPTION OF THE DRAWINGS

Embodiments of the present invention are now described, by way of example, with reference to the accompanying drawings, of which.

DETAILED DESCRIPTION

Figure 1:
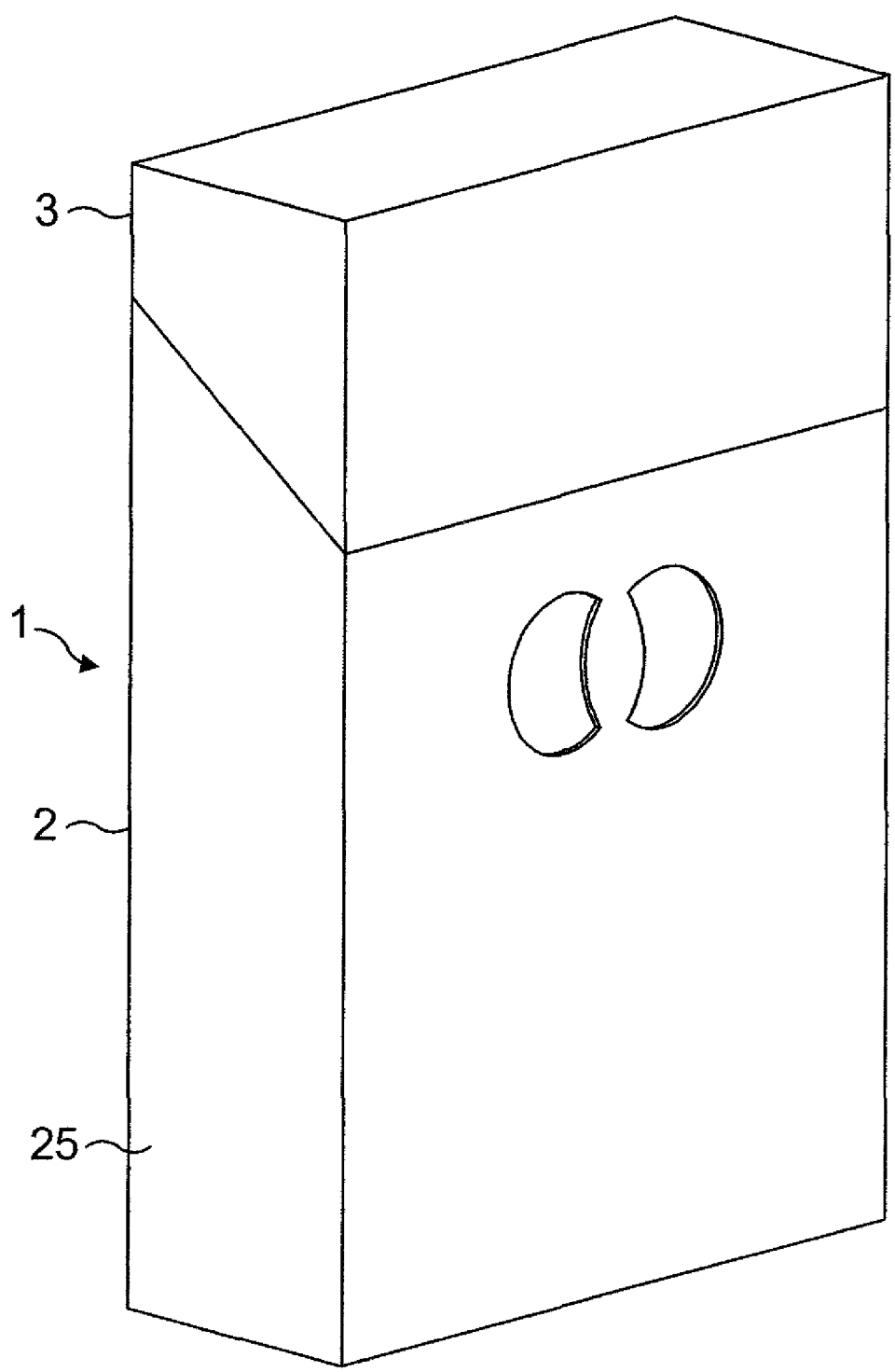
FIG. 1 is a schematic diagram of a pack for tobacco industry products comprising cigarettes.
Figure 2:
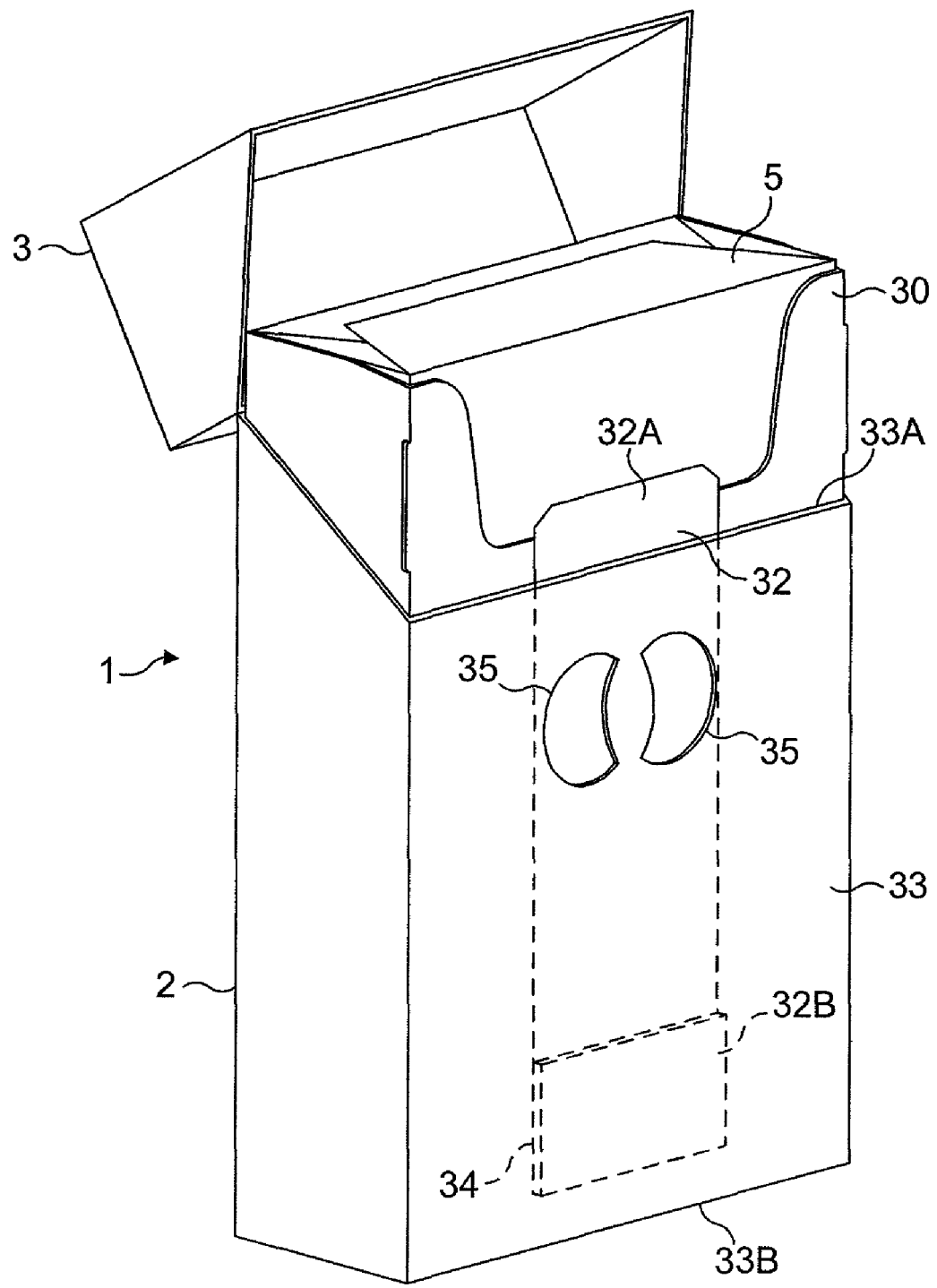
FIG. 2 illustrates the pack of FIG. 1 with its lid open, exposing a pull strip.
Figure 3B:
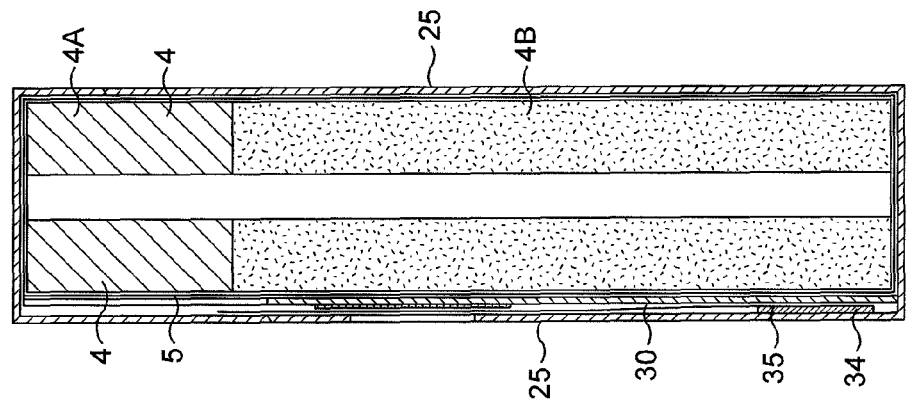
FIG. 3B is a vertical section of the pack illustrated in FIG. 3A along the line B-B.
Figure 3A:
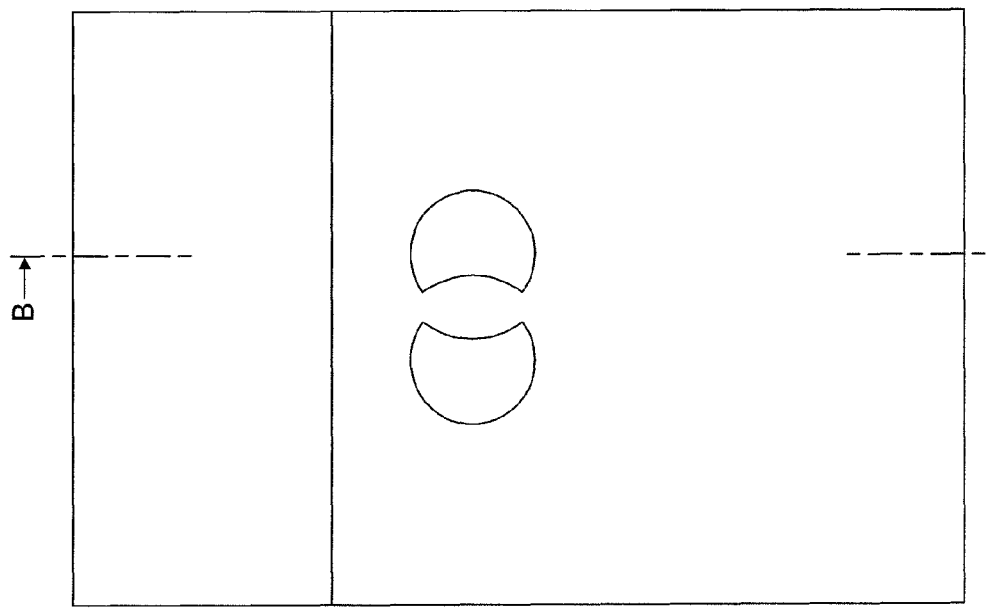
FIG. 3A is a front elevational view of the pack illustrated in FIG. 1.

Referring to FIGS. 1, 2 and 3, a generally rectangular pack 1 comprises a main body 2 with a hinged lid 3 containing two rows of filter tipped cigarettes 4 which each have a tobacco rod 4A and filter tip 4B. The cigarettes 4 may be impregnated with a flavourant such as menthol during manufacture and are contained in a wrapper 5 such as a metallic foil to keep them fresh. The cigarettes within wrapper 5 are contained within an inner frame 30 that fits within outer shell 25 of the main body 2. The inner frame 30 may be made of a generally porous card material whereas the outer shell 25 may be heavily printed and embossed, rendering it generally impermeable, which assists in retaining flavourant in the tobacco of the cigarettes.

Also the pack 1 may be wrapped in a cellophane wrapper, not shown, to seal the pack.

An elongate, generally rectangular, flexible pull strip 32 made of card or plastics material is disposed on front face 33 of the pack 1, between the inner frame 30 and outer shell 25. The pull strip 32 has a manually grippable end 32A that is revealed when the lid 3 is open, protruding above upper edge 33A of the front face 33 of the main body 2.

The pull strip 32 extends towards the bottom edge 33B of the front face of the main body 2. The region 32B of the lowermost end of the pull strip 32 overlies a carrier in the form of a pad 34 impregnated with liquid that may comprise a flavouring substance or flavourant, which is attached to the inside of the front face 33 of the main body. The pad 34 may be made of an adsorbent paper, card or the like. The pad 34 may be glued to the inside of front face 33 and may include a non porous membrane to prevent flavourant being absorbed into the front face 33.

The unglued surface 35 of the pad 34 is covered by the pull strip 32 in region 32B, which may be lightly glued or otherwise releasably attached to one another. The region 32B of the pull strip acts as a barrier to prevent ingress of the liquid from the pad 34 into inner frame 30 when the pull strip is configured as shown in FIGS. 2 and 3.

The outer face 33 of the pack 1 includes an aperture configuration 35 that may be in the form of a distinctive logo, which exposes a portion of the pull strip 32 so as to render the portion of the strip visible from outside the pack 1. A portion of the inner frame 30 that lies beneath the aperture configuration 35 can be of a different visual appearance to the portion of the pull strip that is visible through the aperture configuration 35, and may be of a different colour to the colour of the pull strip.

Figure 4:
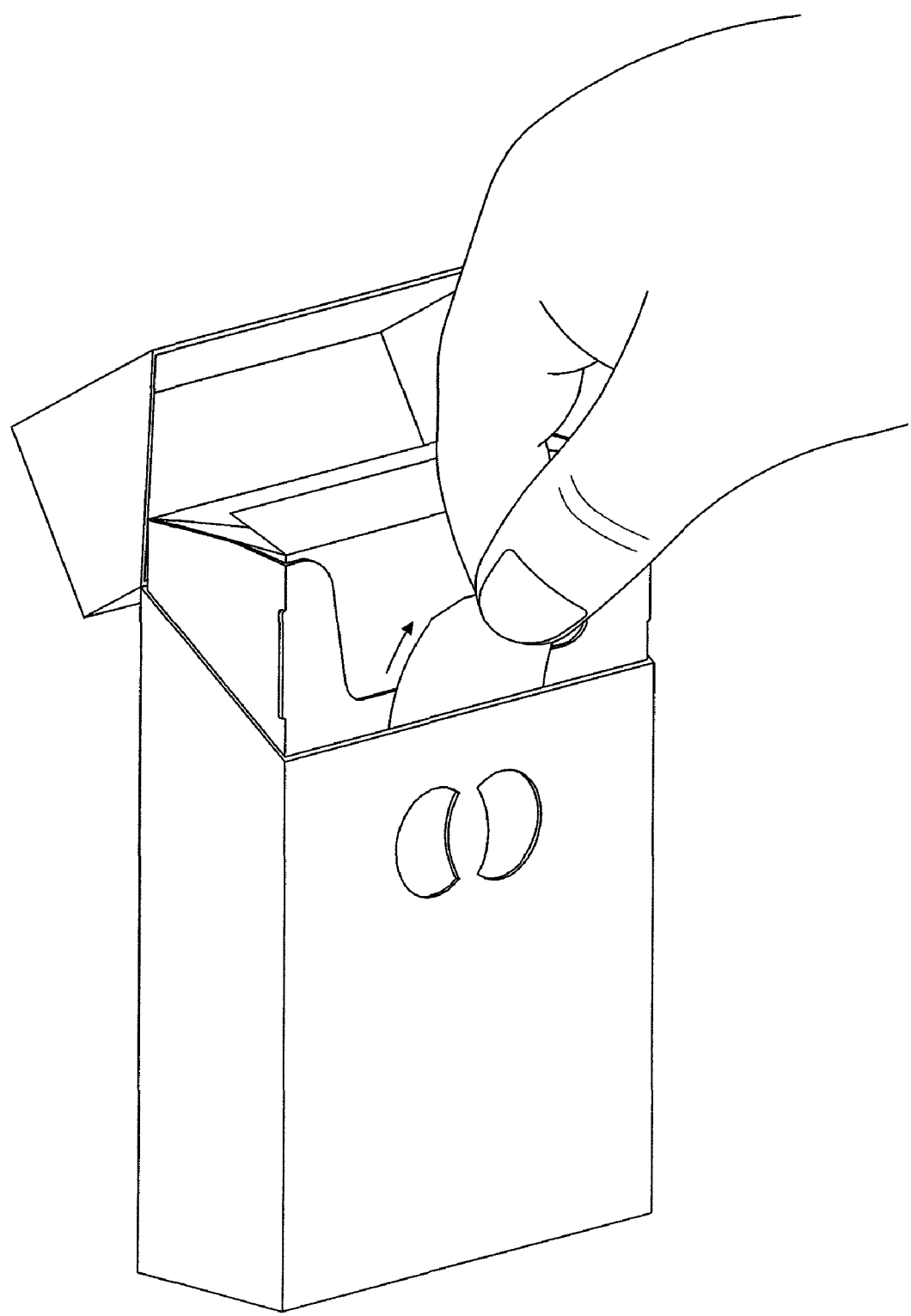
FIG. 4 is a perspective view of the pack of FIG. 1, with the lid open and the pull strip in the process of being removed.
Figure 5:
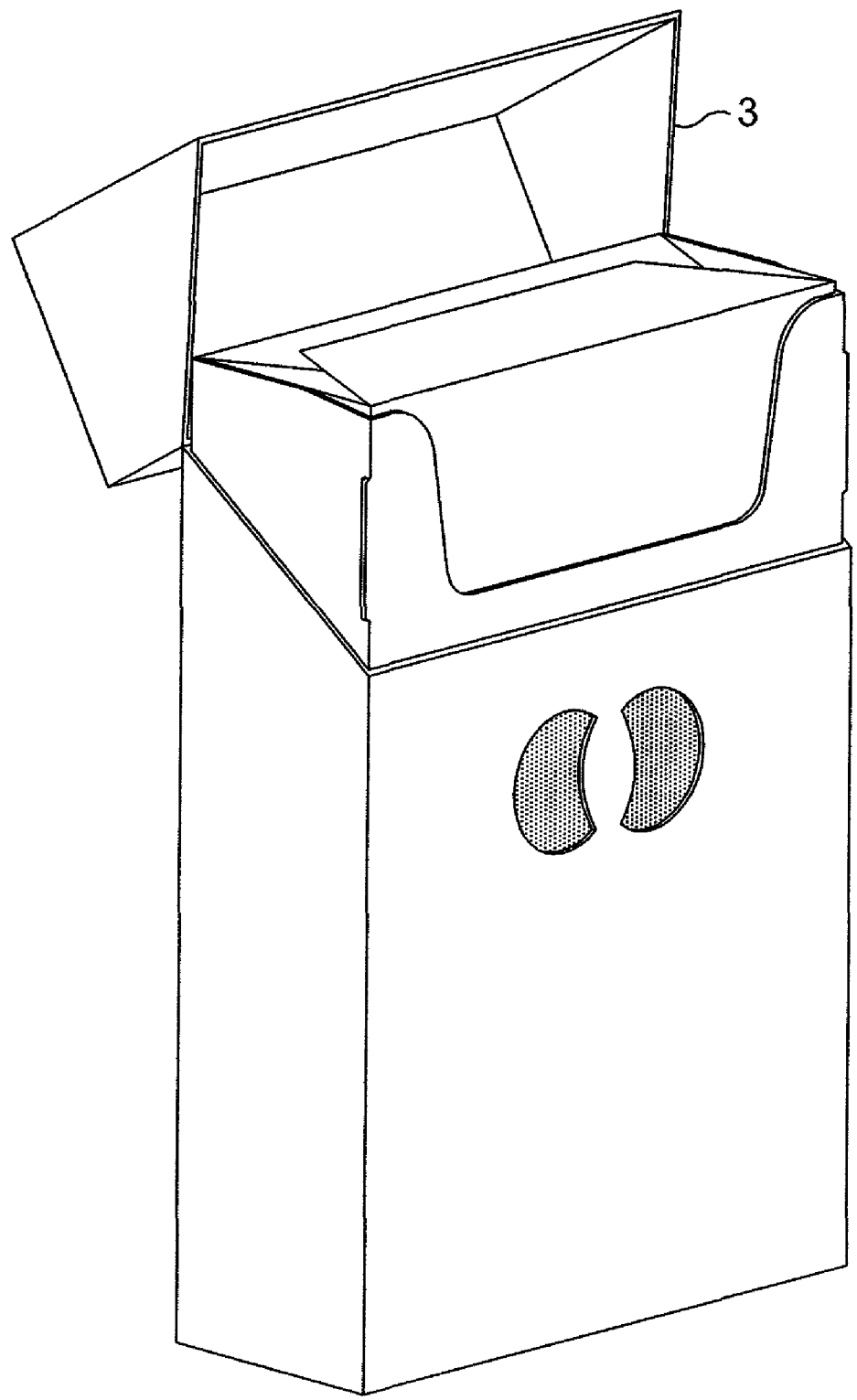
FIG. 5 illustrates the pack of FIG. 4 with the pull strip removed and the lid open.
Figure 6:
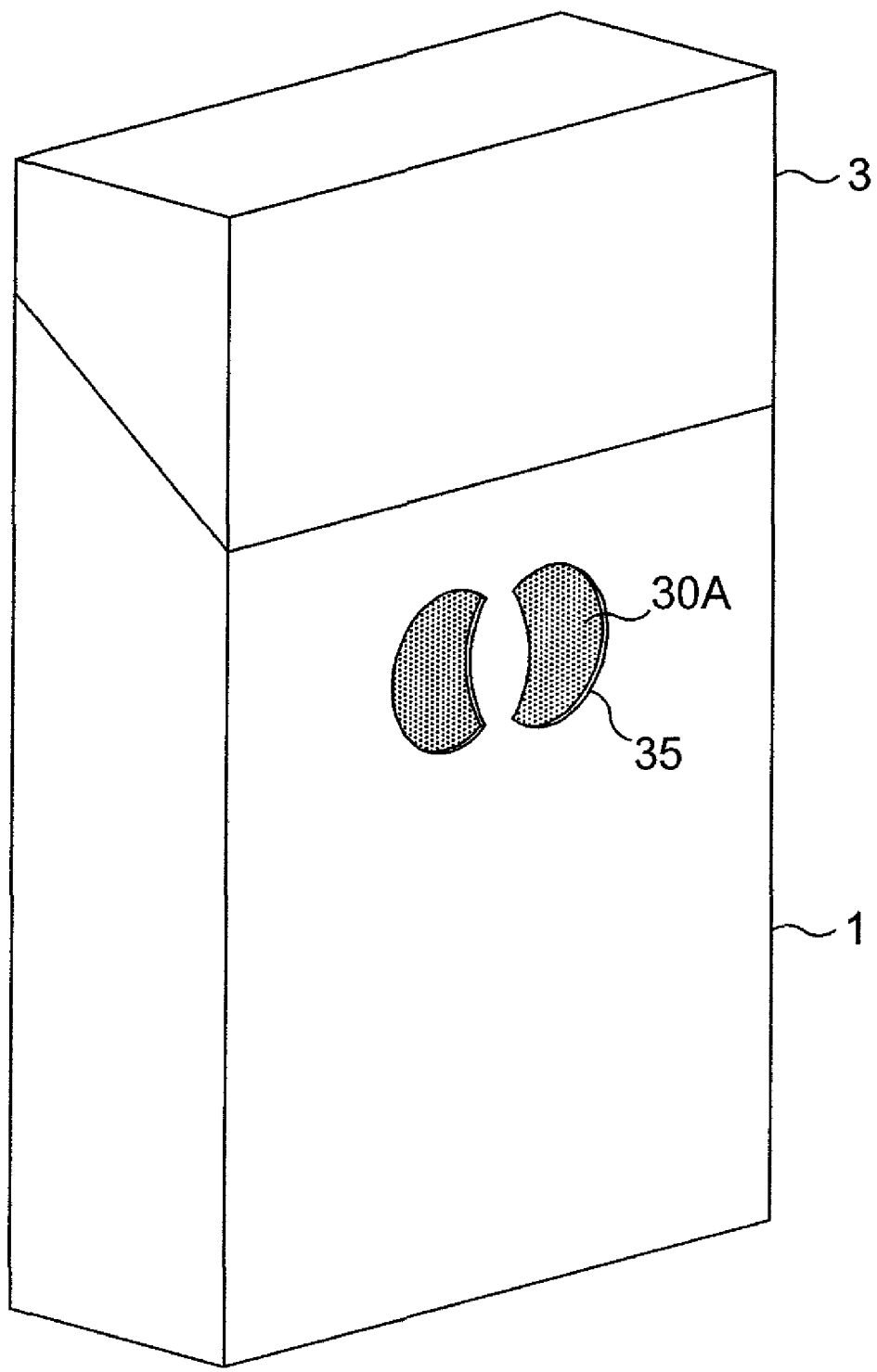
FIG. 6 illustrates the pack of FIG. 5 with the pull strip removed and the lid closed.

The use of the pull strip is illustrated in FIGS. 4, 5 & 6. When the pad 34 is impregnated with a flavourant, removal of the pull strip can be used to replenish or introduce the flavourant from the pad 34 into the cigarettes 4 within the pack 1. To this end, the user opens lid 3 and manually removes the pull strip 32 as illustrated in FIG. 4. The pull strip 32 is consequently removed from adherence with flavourant-impregnated pad 34, with the result that the flavourant can become absorbed into the inner frame 30 which can act as a wick to deliver the flavourant to the tobacco rods 4B and become absorbed in them. Thus, if the pack contains menthol cigarettes, the pad 34 may be impregnated with a menthol containing liquid, which is used to replenish the menthol flavourant in the cigarettes, for example when the pack 1 has been opened previously and some the menthol flavourant provided during manufacture of the cigarettes has dissipated from them. Alternatively the pad may be used to introduce a different flavourant or liquid into the cigarettes, which need not necessarily have been flavoured during manufacture.

The flavourant may be delivered through the inner frame 30 which acts as a wick, preferentially to different parts of the cigarettes, for example preferentially to the tobacco rods 4B rather than the filter tips 4A, due to the filter tips 4A being disposed at the top of the pack, more distant from the pad 34 than the tobacco rods 4B. Moreover, the inner frame 30 may be configured to provide separate wicking paths, not shown, to deliver the liquid from the pad 34 preferentially to different regions of the cigarette tobacco rods. Also, in a modification, a wick, not shown, may be included that is separate from the inner frame 30.

Alternatively the pad 30 may have direct access to the interior of the pack 1 and hence to the tobacco industry products rather than use the inner frame 30 as a wick. To this end the inner frame 30 may be configured to provide direct access from the pad 30 to the cigarettes 4 by being suitably shaped around the pad 30 or including an aperture in the region of the pad.

FIG. 5 illustrates the pack 1 with the strip 32 removed. Region 30A of the inner frame 30 that lies behind the apertures 35 is of a different colour from the pull-strip 32. For example, when a menthol flavourant is disposed in the pad 34, the region 30A may be a green colour so that, when exposed after removal of a pull strip, the colour provides a visual indication that the additional menthol has been introduced into the cigarettes within the pack 1. FIG. 6 illustrates the pack 1 when the lid 3 is closed following the removal of the pull strip 32 with the exposed region 30A showing.

The pack can be manufactured by folding and gluing a first blank to form the outer shell 25 comprising the main body 2 and lid 3, with the pad 34 being pre-impregnated with the liquid flavourant and glued to the inside of the panel of the blank that forms the front face 33 of the pack 1. A modified coupon/insert feeder may be used in an otherwise conventional hinged lid cigarette packing machine to apply the pad 34 to the inner frame. The pull strip 32 is releasably attached to the pad 34. These parts may be attached by means of a hot melt adhesive. The cigarettes 4 are wrapped in the foil wrapper 5 and placed in the inner frame 30, which itself is formed by folding from a second blank of porous card, and the resulting assembly of the cigarettes and inner from is inserted into the outer shell, so that the pull strip 32 is between the inner frame 30 and the outer shell 25. Registration equipment may be employed to ensure that the pad 34 and the pull strip 32 are accurately placed before the outer shell is formed.

Alternatively, the pad 34 may be pre-assembled and glued to the inner frame blank before it reaches the packing machine.

The present invention has been described above with reference to the enhancement of flavouring substances in tobacco industry products, such as menthol or other flavours. However, the present invention can also be applied to the distribution of other aromatic products, water or humectants which may be used to refresh dry and stale products without additional flavouring of the product. Thus the pad 34 may be impregnated with such other aromatic products such as spearmint or peppermint, or water or humectants rather than menthol as described above. Thus the pad can be used to accommodate any suitable substance for altering characteristics of the tobacco industry products when in the pack.

Also the strip 32 which comprises a pull strip could be configured in different ways. For example, the strip could overlie the pad 34 only and have a length of cord attached thereto which could extend into the lid to allow the strip to be removed by pulling the cord.

Other embodiments of the present invention will be envisaged by the skilled person without departing from the scope of the invention as defined in the claims.

The invention claimed is:

1. A pack for tobacco industry products, comprising:
a housing defining an enclosure in which a plurality of tobacco industry products can be accommodated, the housing comprising an outer shell, an inner frame and a lid, and
a carrier disposed in or on a pack, said carrier able to accommodate a substance for altering characteristics of the tobacco industry products within the pack;
wherein the carrier comprises a pad impregnated with the substance, and a removable strip, the pad and the strip being disposed between the outer shell and the inner frame and the strip having a portion extending into the lid wherein when opened, the strip can be gripped manually and removed from engagement with the pad to release the substance from the pad into the pack.

2. The pack according to claim 1 wherein the pad is attached to the outer shell, and a membrane is provided between the outer shell and the pad to prevent the substance in the pad from passing into the outer shell.

3. The pack according to claim 1 including an aperture configuration in the outer shell overlying the strip to provide a visual indication of whether the strip has been removed from the pack.

4. The pack according to claim 3 wherein the inner frame is of a different appearance from the strip in a region underlying the aperture configuration in the outer shell.

5. The pack according to claim 1, including a wick to convey the substance from the pad within the enclosure.

6. The pack according to claim 5, wherein the wick comprises a portion of the housing.

7. The pack according to claim 5, wherein the wick is disposed to direct to the substance released from the carrier to a predetermined portion of the enclosure.

8. The pack according to claim 7, wherein tobacco industry products are contained in the pack that comprise filter tipped smoking articles, and the predetermined portion of the enclosure is disposed distally from the end for the filters.

9. The pack according to claim 1, wherein the inner frame is permeable to the substance accommodated in the carrier.

10. The pack according to claim 1 wherein the substance accommodated in the carrier comprises at least one of a flavouring substance and a substance to refresh dry and stale products without additional flavouring thereof.

11. The pack according to claim 1 wherein the substance accommodated in the carrier is menthol.

12. The pack according to claim 1, wherein the substance accommodated in the carrier is water.

13. The pack according to claim 1 wherein the pack contains smoking articles.

14. The pack according to claim 1 wherein the pack contains menthol flavoured cigarettes.

15. A kit for forming a pack for tobacco industry products, comprising:
a first blank foldable to form an outer shell for a pack having an openable lid, and a second blank foldable to form an inner frame for containing tobacco industry products, to be received within the outer shell; and
a carrier to be disposed between the inner frame and outer shell, said carrier being arranged to accommodate a substance for altering characteristics of the tobacco industry products when in the pack, the carrier comprising a pad to be impregnated with the substance and a removable strip, attached to the carrier so that when removed, the substance is released into the pack from the carrier, the strip having a portion to extend into the lid so that when opened, the strip can be gripped manually and removed from engagement with the pad to release the substance from the pad into the pack.

16. A method of manufacturing a pack for tobacco industry products, comprising:
forming a housing defining an enclosure in which a plurality of tobacco industry products can be accommodated, the housing comprising an outer shell, an inner frame and a lid, and
providing a carrier disposed in or on a pack, said carrier for a substance for altering characteristics of the tobacco industry products when in the pack, the carrier comprising a pad impregnated with the substance, and a removable strip attached to the carrier, the pad and the strip being disposed between the outer shell and the inner frame and the strip having a portion extending into the lid so that when opened, the strip can be gripped manually and removed from engagement with the pad to release the substance from the pad into the pack.

17. The method according to claim 16 including attaching the carrier to a blank and folding the blank to form the inner frame.

18. The method according to claim 16 including gluing the carrier to the inner frame.

* * * * *